(12) United States Patent
Helfer et al.

(10) Patent No.: US 10,195,430 B2
(45) Date of Patent: Feb. 5, 2019

(54) STIMULATION BRACE

(71) Applicant: DJO, LLC, Vista, CA (US)

(72) Inventors: Sylvain Helfer, Grandvaux (CH); Klaus Schonenberger, Vufflens-la-Ville (CH); Felix Buhlmann, Lausanne (CH)

(73) Assignee: DJO, LLC, Vista, CA (US)

( * ) Notice: Subject to any disclaimer, the term of this patent is extended or adjusted under 35 U.S.C. 154(b) by 693 days.

(21) Appl. No.: 14/834,308

(22) Filed: Aug. 24, 2015

(65) Prior Publication Data

US 2016/0074656 A1 Mar. 17, 2016

Related U.S. Application Data

(63) Continuation of application No. 12/865,988, filed as application No. PCT/IB2009/050460 on Feb. 5, 2009, now Pat. No. 9,114,257.

(30) Foreign Application Priority Data

Feb. 5, 2008 (EP) ..................................... 08151073

(51) Int. Cl.
*A61N 1/36* (2006.01)
*A61F 5/01* (2006.01)
(Continued)

(52) U.S. Cl.
CPC .............. *A61N 1/36014* (2013.01); *A61F 5/01* (2013.01); *A61N 1/048* (2013.01); *A61N 1/0452* (2013.01); *A61N 1/0464* (2013.01); *A61N 1/0472* (2013.01); *A61N 1/0484* (2013.01); *A61N 1/0492* (2013.01); *A61N 1/321* (2013.01); *A61N 1/36003* (2013.01); *A61N 1/36021* (2013.01);
(Continued)

(58) Field of Classification Search
CPC .... A61F 5/0104–5/0118; A61F 5/0123–5/013; A61F 2005/0102–2005/0197; A61N 1/36003; A61N 1/36014; A61N 1/22; A61N 1/321; A61N 1/0452; A61N 1/0456; A61N 1/0464; A61N 1/0468; A61N 1/0484
USPC ...................... 602/2, 23–26, 62; 601/15, 21; 607/48–50, 148–148, 152
See application file for complete search history.

(56) References Cited

U.S. PATENT DOCUMENTS 3,911,910 A 10/1975 Oesau
4,586,495 A 5/1986 Petrofsky
(Continued)

FOREIGN PATENT DOCUMENTS

EP 0 302 148 2/1989
EP 0302148 2/1989
(Continued)

OTHER PUBLICATIONS

Post et al., 2000, E-broidery: design and fabrication of textile-based computing, IBM Systems Journal, 39(3-4):840-860.
(Continued)

*Primary Examiner* — Kari Rodriquez
(74) *Attorney, Agent, or Firm* — Knobbe Martens Olson & Bear LLP

(57) ABSTRACT

A device for the treatment of the body of a wearer comprising an orthopedic brace combined with at least one electrically active zone to stimulate the body of the wearer of the brace.

13 Claims, 8 Drawing Sheets

(51) Int. Cl.
*A61N 1/04* (2006.01)
*A61N 1/32* (2006.01)
*A61N 1/20* (2006.01)
*A61N 1/22* (2006.01)

(52) U.S. Cl.
CPC ............... *A61N 1/205* (2013.01); *A61N 1/22* (2013.01); *A61N 1/326* (2013.01)

(56) References Cited

U.S. PATENT DOCUMENTS

| | | | |
|---|---|---|---|
| 4,697,808 | A | 10/1987 | Larson et al. |
| 4,796,631 | A | 1/1989 | Grigoryev |
| 4,889,111 | A | 12/1989 | Ben-dov |
| 5,121,747 | A | 6/1992 | Andrews |
| 5,263,481 | A | 11/1993 | Axelgaard |
| 5,330,477 | A | 7/1994 | Crook |
| 5,397,338 | A | 3/1995 | Grey et al. |
| 5,476,441 | A | 12/1995 | Durfee et al. |
| 5,562,707 | A * | 10/1996 | Prochazka ............... A61N 1/05 607/2 |
| 5,628,722 | A * | 5/1997 | Solomonow .......... A61F 5/0123 128/898 |
| 5,766,236 | A | 6/1998 | Detty et al. |
| 6,279,159 | B1 | 8/2001 | Alhbaumer et al. |
| 6,607,500 | B2 | 8/2003 | Da Silva et al. |
| 7,162,305 | B2 | 1/2007 | Tong et al. |
| 9,114,257 | B2 | 8/2015 | Helfer et al. |
| 2002/0032475 | A1 | 3/2002 | Arbel |
| 2004/0173220 | A1 | 9/2004 | Harry et al. |
| 2004/0243196 | A1 | 12/2004 | Campos et al. |
| 2007/0112394 | A1 | 5/2007 | Nathan et al. |
| 2007/0197946 | A1 | 8/2007 | Gilmour |
| 2008/0177168 | A1 | 7/2008 | Callahan et al. |

FOREIGN PATENT DOCUMENTS

| | | |
|---|---|---|
| EP | 0 506 398 | 3/1991 |
| EP | 0506398 | 3/1991 |
| EP | 0 553 517 | 8/1993 |
| EP | 0553517 | 8/1993 |
| EP | 1 136 096 | 9/2001 |
| EP | 1136096 | 9/2001 |
| GB | 2426930 | 12/2006 |
| JP | 2002/200104 | 7/2002 |
| JP | 2002-200104 | 7/2002 |
| JP | 2002/191707 | 10/2002 |
| JP | 2002-191707 | 10/2002 |
| WO | WO 94/28966 | 12/1994 |
| WO | WO 1994/28966 | 12/1994 |
| WO | WO 96/18364 | 6/1996 |
| WO | WO 1996/18364 | 6/1996 |
| WO | WO 98/43560 | 10/1998 |
| WO | WO 1998/43560 | 10/1998 |
| WO | WO 01/03768 | 1/2001 |
| WO | WO 2001/03768 | 1/2001 |
| WO | WO 02/060311 | 8/2002 |
| WO | WO 2002/060311 | 8/2002 |
| WO | WO 02/092164 | 11/2002 |
| WO | WO 2002/092164 | 11/2002 |
| WO | WO 03/024371 | 3/2003 |
| WO | WO 2003/024371 | 3/2003 |
| WO | WO 05/007029 | 1/2005 |
| WO | WO 2005/007029 | 1/2005 |
| WO | WO 06/060934 | 6/2006 |
| WO | WO 2006/060934 | 6/2006 |
| WO | WO 07/057899 | 5/2007 |
| WO | WO 2007/057899 | 5/2007 |
| WO | WO 07/093941 | 8/2007 |
| WO | WO 2007/093941 | 8/2007 |

OTHER PUBLICATIONS

International Search Report for application No. PCT/IB09/050460, dated Jun. 17, 2009.
Extended European Search Report dated Jul. 27, 2016 in related European patent application No. 16164833.2.

* cited by examiner

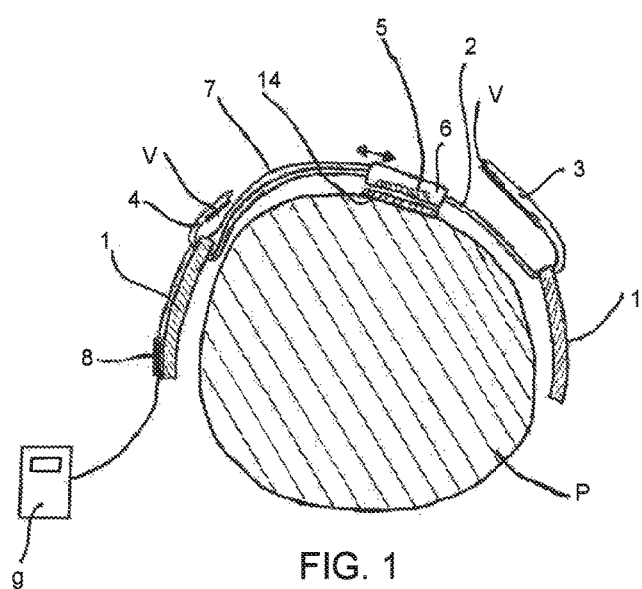
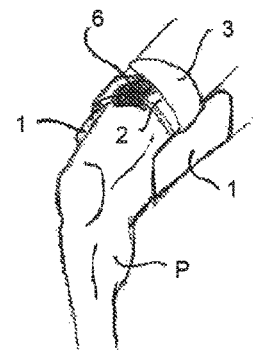
FIG. 1A
FIG. 1
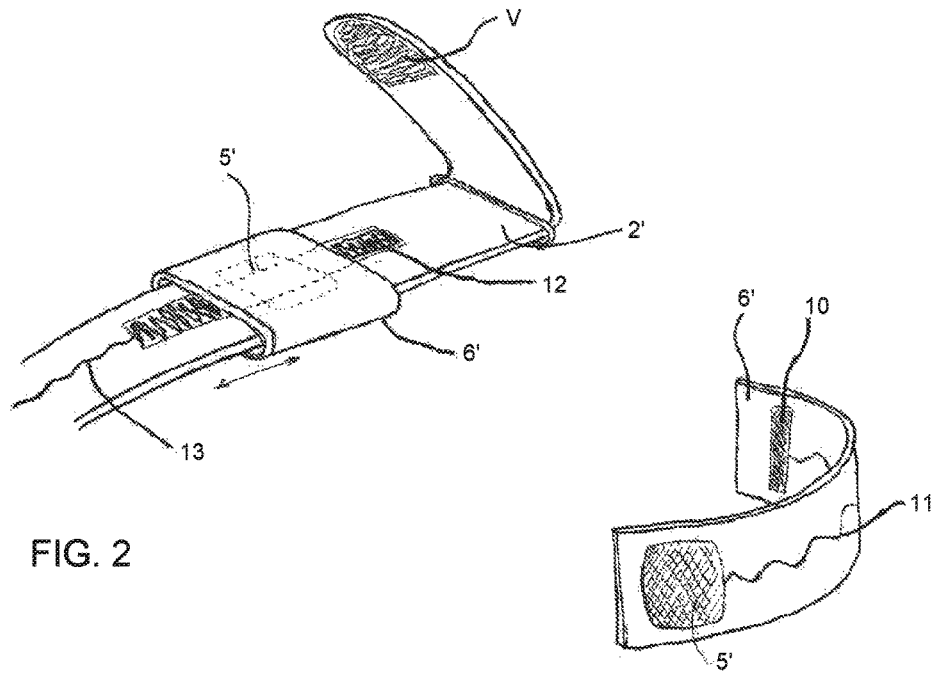
FIG. 2
FIG. 3

STIMULATION BRACE

RELATED APPLICATIONS

This application is a continuation of U.S. application Ser. No. 12/865,988, filed Mar. 31, 2011, which is a national stage filing under 35 U.S.C. § 371 of International Application No. PCT/IB2009/050460, filed Feb. 5, 2009, which claims the benefit of European Application No. 08151073.7, filed Feb. 5, 2008, the contents of which are incorporated by reference in their entirety. International Application No. PCT/IB2009/050460 was published under PCT Article 21(2) in English.

TECHNICAL FIELD

The present invention concerns a stimulation brace. In particular, the present invention concerns a brace that is capable of carrying out an electrical stimulation of the body part on which the brace is used.

BACKGROUND ART

Brace are well known per se in the art. An orthopaedic brace (also orthosis or orthotic) as commonly defined in the art is a device used to:
- immobilize a joint or body segment,
- restrict movement in a given direction,
- assist movement,
- reduce weight-bearing forces, or
- correct the shape of the body.

Usually, the last purpose listed above is what persons call in common speech a brace, whether it is made from elastic neoprene or a stiffer, more restrictive construction such as hard plastic or metal. An orthotic is most often understood to be a somewhat flexible device, often an insert for shoes, to correct leg length, fallen arches (flat feet), or some other foot problem.

Often the older type of leg brace is meant, constructed of steel side bars and ring, with spurs which fit into a metal tube in the heel of an adapted shoe or boot, and with straps and bands around the leg to hold the splint in position. The straps can be secured with VELCRO™ but many patients prefer buckles. This type of braces can either be non-weight relieving or, by slight lengthening, made to relieve weight by raising the heel of the foot away from the heel of the shoe or boot. These splints have to be individually made by an orthotist or appliance maker in order to closely fit the particular contours of the leg being supported. Of course, other types of braces are known which are used on other body parts.

On the other hand, the electrical stimulation of the body is a technique that is also well known in the art for example for stimulation, pain management, edema reduction, muscle or vascular rehabilitation, bone growth stimulation etc. This technique usually implies the use of electrically active zones, for examples electrodes, linked to a stimulator (portable or not) that contains a stimulation program to be applied to a person (i.e. body part for example).

In a further technology development, one has started to combine the use of a brace with electrodes. A typical example of such a device is given in U.S. Pat. No. 3,911,910 which discloses an electro-splint for relieving involuntary muscular spasticity. More specifically, this device comprises a splint structure for attachment to a body limb combined with skin attachable electrodes for attachment to skin zones overlying the trigger points of body muscle that control angular displacement of the associated limb portion.

Other prior art in the field includes the following publications: WO 94/28966, U.S. Pat. No. 5,397,338, WO 96/18364, U.S. Pat. No. 5,628,722, U.S. Pat. No. 5,766,236, WO 98/43560, US2002/0032475, WO 02/060311, U.S. Pat. No. 6,607,500, US 2004/0243196, U.S. Pat. No. 4,586,495, EP 0 302 148, U.S. Pat. No. 4,697,808, U.S. Pat. No. 4,796,631, U.S. Pat. No. 5,121,747, EP 0 506 398, U.S. Pat. No. 5,476,441, EP 1 136 096, WO 02/092164, U.S. Pat. No. 7,162,305, US 2007/0112394, WO 2007/057899, WO 2007/093941, US 2007/197946, GB 2 426 930, WO 02/092164, WO2005/007029, WO 01/03768, JP 2002 200104, JP 2002 191707 and U.S. Pat. No. 5,628,722.

In the specific field of bone growth and stimulation, the following publications can be considered as background: U.S. Pat. No. 4,889,111, EP 0 553 517, U.S. Pat. No. 5,330,477 and WO 03/024371.

SUMMARY OF THE INVENTION

It is an aim of the present invention to improve the known devices.

More specifically, it is an aim of the present invention to provide a device that is easy to use.

Another aim of the present invention is to provide a device that is able at the same time to be used as a brace and also as a stimulating device for electrical stimulation of the user.

It is a further aim of the present invention to provide a device that allows an easy and adjustable placement of electrically active zone (such as electrodes). This placement will be possible horizontally along the brace's stripe and vertically perpendicularly to the stripes.

A further aim of the present invention is to provide a device that allows an easy replacement of electrically active zones.

Another aim is to include on the brace electrically active zones or sensors that are able to carry out measurements on the body, for example: EMG (electromyography), brace position, angle, number of flexions, etc.

Another aim is to make the brace more compliant for a practitioner. It will be possible to record values measured by the sensors in order to evaluate the accurate use of the brace and the state of recovery of the body part that is being treated via appropriate analysing and evaluation means.

In the present application, it is understood that the notion of brace covers in a general manner all types of braces, that is for example soft braces, rigid braces, splints etc and other similar devices that can be worn by a user/patient.

BRIEF DESCRIPTION OF THE DRAWINGS

The present invention will be best understood from the following description of several illustrative embodiments and from the drawings in which FIG. 1 illustrates a first embodiment of the device according to the invention;

FIG. 1A is an illustrative implantation of the embodiment of FIG. 1;

FIG. 2 illustrates a variant of the first embodiment;

FIG. 3 illustrates a detail of an element of FIG. 2;

DETAILED DESCRIPTION OF THE PREFERRED EMBODIMENT

Figure 2B:
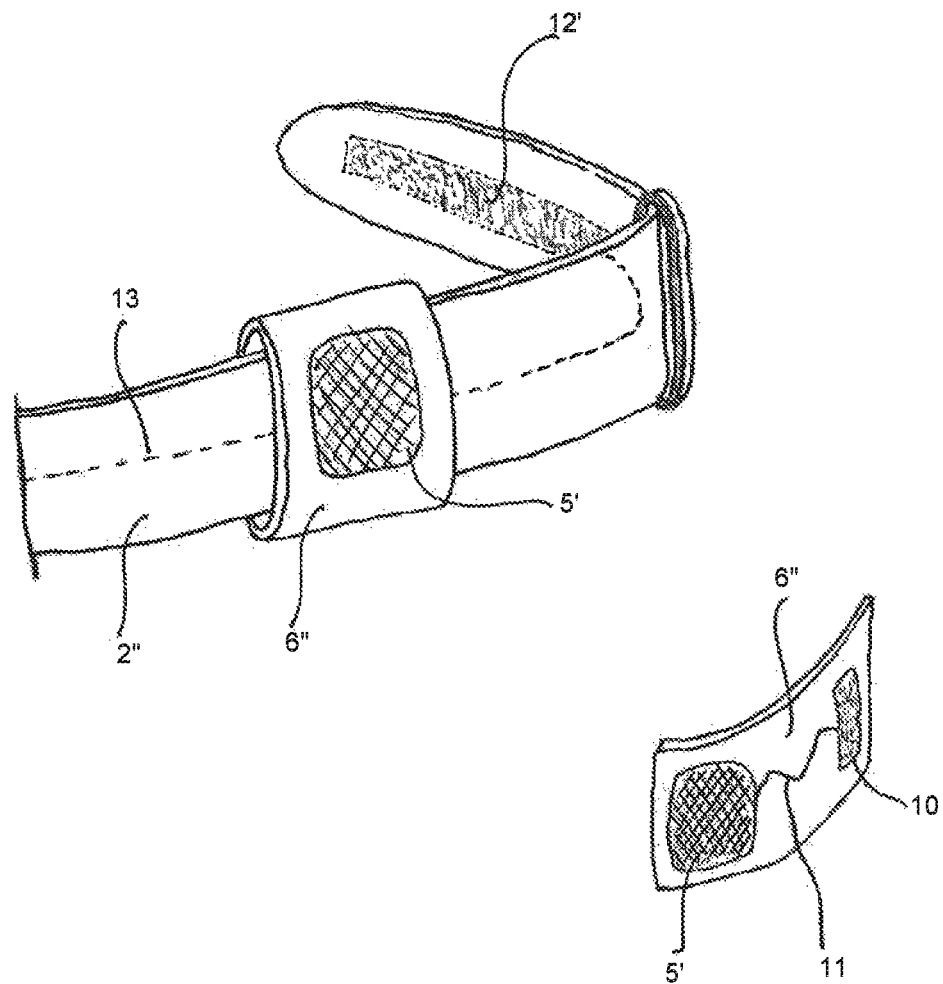
FIG. 2b illustrates a variant of the first embodiment with a conductive Velcro®.

In FIG. 1, a first illustrative embodiment of the device according to the invention is represented. This figure is a cut view of the embodiment represented at FIG. 1A.

In the first embodiment, the brace 1 is for example made of metal (other material being possible of course), and is placed on a patient's leg or arm or any body part that has to be treated (such as leg, arm, wrist, elbow, shoulder etc.). The example of FIGS. 1 and 1A illustrates as an example the application to the leg P of a person. Between the two ends of the brace 1, there is a strap 2 which is for example used to properly apply the brace on the limb of the user (see for example FIG. 1A).

The strap has two ends 3, 4, at least one of said ends being detachable from the brace to allow adjustment to the user. In FIG. 1, both ends 3, 4 are detachable and are attached to the brace through an opening (slot) in the brace and through Velcro™ means V or equivalent means.

In the embodiment illustrated in FIG. 1, the electrically active zone 5 can be embroidered on a support 6 for example made of fabric. Of course, the embroidering is only one example for realizing the electrically active zone 5. Other ways can be imagined and used in an equivalent manner. For example the active zone 5 could be made of an electrically active patch (carbon sheet or any other conductive material) attached to the support 6 or to the strap 2.

Preferably, the support 6 is made of a fabric strap that is folded and attached to form a "loop patch" that is then mounted on the strap 2. In this way, the support 6 can be displaced at will along the strap 2 to be at the desired position. Of course, it is also possible to use a fixed support or to provide the electrically active zone directly on the strap 2.

In addition, a conductive wire 7 is connected to the electrically active zone 5, said wire 7 running along the brace to a an electrical contact 8 for connection to a stimulator 9. Preferably, the connection of the wire to the active zone 5 is made by a detachable connector. Similarly, the connection of the stimulator 9 to the electrical contact 8 can de a detachable connection. In a variant applicable to all the embodiments described herein, the stimulator 9 may be connected and attached directly to the brace 1 itself.

FIGS. 2, 2b and 3 illustrate a variant wherein the wire 7 of FIG. 1 is replaced by equivalent means. In this variant, the support 6' is also made for example of a strap of fabric with a first embroidered electrically active zone 5'. In addition, the support 6' comprises a second embroidered electrically active zone 10 on the other side of the strap 6' with respect to the first zone 5'. Both zones 5' and 10 are electrically connected to each other by a conductive wire 11. The wire 11 may be a wire with an outer non-conductive isolation, and the contact between the wire 11 and the zones 5' and 10 is preferably made when embroidering the zones 5' and 10 by direct stitching through the isolation of the wire 11.

In addition, in this variant, the strap 2' (corresponding to the strap 2 of FIG. 1) is modified in the following manner. It also comprises an embroidered electrically active zone 12 which is connected to a wire 13 preferably having a non-conductive isolation used for connection to a stimulator (not represented in FIGS. 2 and 3). As with the support 6', the electrical connection between wire 13 and zone 12 is for example made by direct stitching through the isolation of the wire 13 when embroidering the zone 12. An example of this embroidering technique is disclosed in WO 2006/060934. Of course, the electrically active zones may be realized by other techniques than embroidering or other equivalent means.

As illustrated in FIG. 2, the support 6' is placed on the strap 2' with the zone 10 of the support 6' contacting the zone 12 of the strap 2' to allow the stimulation signal to be transferred from the stimulator to the electrically active zone 5'.

Of course, it is also possible to combine the use of a wire (as described in reference to FIG. 1) and the variant of FIGS. 2 and 3 (use of several electrically active zones) according to circumstances.

In FIG. 2b, the strap 2" comprises a zone with a conductive attachment means 12', for example a conductive Velcro® connected to a leadwire 13. The support 6" comprises the electrode 5' which is connected via the leadwire 11 to a conductive zone 10' made for example of a conductive Velcro® cooperating with the attachment means 12' for allowing the electrical stimulation to reach the electrically active zone 5'.

Also, it is possible in a variant to embroider the electrically active zones directly on the strap rather than on a support (such as support 6 or 6').

In further variants, it is possible to place the electrically active zones on other parts of the brace (for example on cushions of the brace). In this case, the electrically active zone can be directly embroidered on said cushions or on a support that is placed over said cushions. As described hereabove, the electrical connection to the stimulator may be realized by wires or by embroidered contacts.

Preferably, in addition, one uses a gel electrode 14 (see FIG. 1), for example having one or several conductive gel layers, or conductive paste that is placed between the electrically active zones and the surface of the skin of the user.

As mentioned above, the mentioned embroidered electrically active zones can be made of other equivalent means that are non-embroidered, such as electrically conductive elements, sheets of appropriate materials suitable for the intended use etc. In this case, these electrically conductive element can be attached to the brace (or part of the brace such as a strap etc) by any appropriate means, such a gluing or other equivalent means.

A second embodiment of the invention is described with reference to FIGS. 4 to 7B. In this embodiment, the electrically active zone is more integrated in the brace. More specifically, the brace 20 (see FIG. 4) comprises an opening 21 (or window) where an electrically active zone has to be placed. In addition, the brace 20 comprises a strap 22 in the region of the opening 21 the use of which will be explained later.

Figure 4:
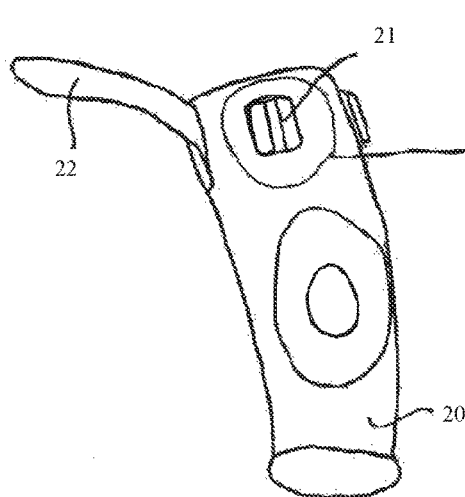
FIG. 4 illustrates a second embodiment of the invention.
Figure 4A:
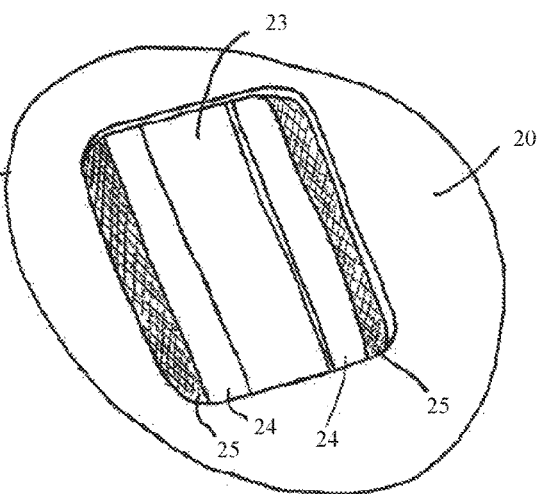
FIG. 4A illustrates a detail of FIG. 4.

In FIG. 4A, a detail of the opening 21 is illustrated. In this opening 21, one shows the skin 23 of the user, a first non conductive layer 24 and a conductive layer 25 (for example an embroidered conductive layer or a soft conductive layer, for example a carbon layer, or another equivalent conductive layer).

Figure 5:
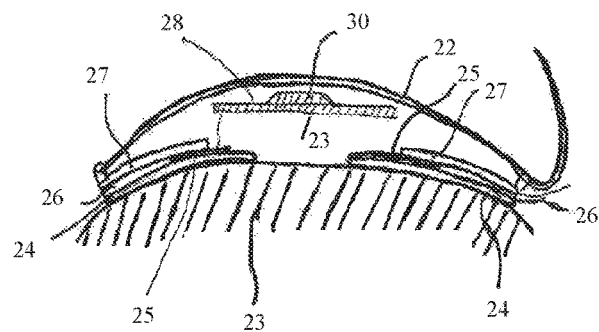
FIGS. 5 and 6 illustrate a cut view of the second embodiment.
Figure 6:
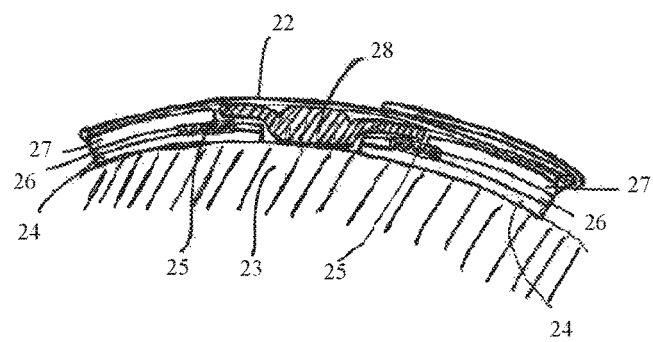

In FIGS. 5 and 6 (illustrating respectively an open configuration and a closed configuration), the layers 24, 25 described with reference to FIG. 4A are illustrated in a cut view for a better understanding. Over the skin 23 of the user, there is the first non-conductive layer 24, then the conductive layer 25, with a neighbouring layer 26 and a top layer 27. All these layers 24-27 are in fact part of the brace 20.

In addition, in FIGS. 5 and 6, one has represented the electrically active zone 28 (for example a gel electrode having one or several conductive gel layers, or conductive paste) that is placed over the opening for the electrical treatment of the user/wearer. This electrically active zone 28 comprises a flat part 29 and a local thickness 30, the use of which will be explained later.

A represented in FIGS. 5 and 6, the electrically active zone 28 is placed over the opening 21 and in contact with the conductive parts 25 which are on both sides of the opening 21. The strap (when being attached) passes over the electrode 28 and presses said electrically active zone 28 into the opening thereby ensuring the contact with the parts 25. In addition, because of the local thickness 30, the electrically active zone 28 is deformed and pushed into the opening 21 in order to contact the skin 23 of the wearer, as is illustrated in FIG. 6. In such a position, it is then possible to carry out a treatment (for example an electrical stimulation) of the wearer.

Figure 7A:
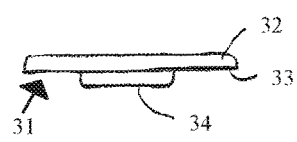
FIGS. 7, 7A and 7B illustrate a variant of the second embodiment.
Figure 7B:
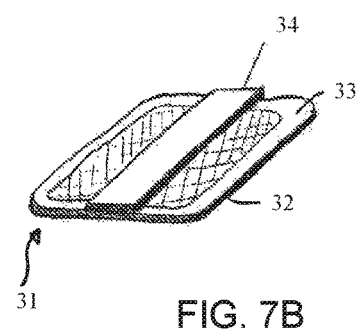
Figure 7:
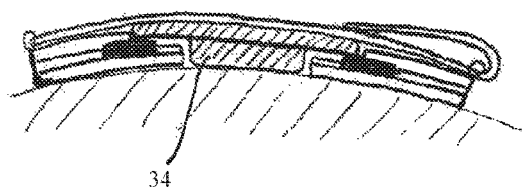

FIGS. 7, 7A and 7B illustrate a variant of the second embodiment. In this variant, the electrically active zone 31 is of a different type. The electrically active zone 31 is made of a non conductive backing 32 carrying a conductive layer 33. In addition, it comprises a strip of conductive gel 34 which is used to contact the skin of the wearer. The system according to this variant is represented in a mounted state in FIG. 7. In this variant, the brace is similar to the one of FIGS. 4-6 and reference is made to its description hereabove.

Figure 7C:
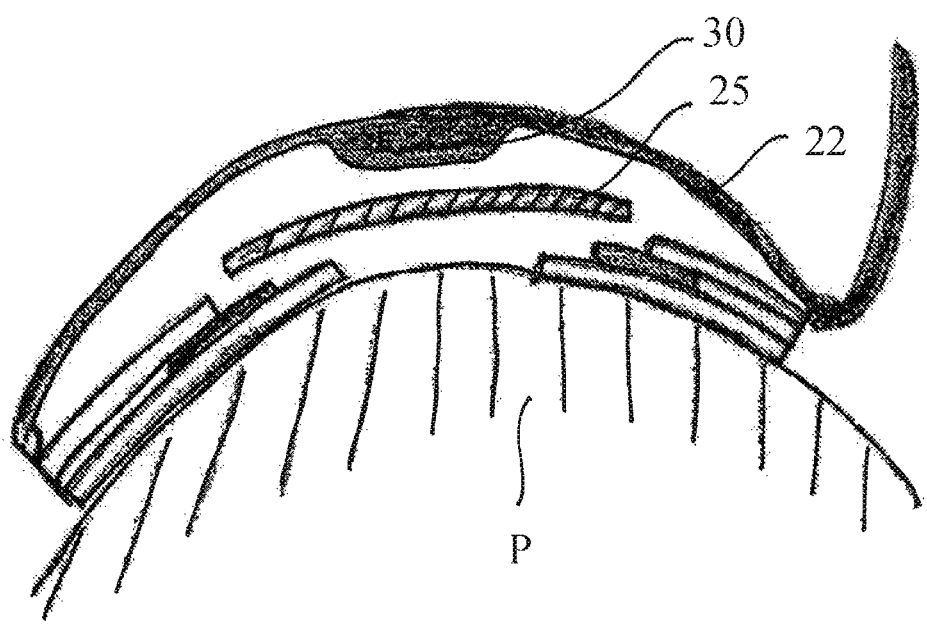
FIG. 7C illustrates a variant of the second embodiment
Figure 7C:
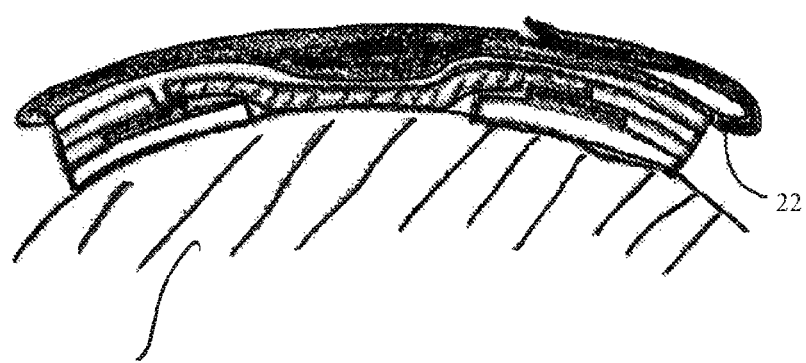
Figures 8, 8A:
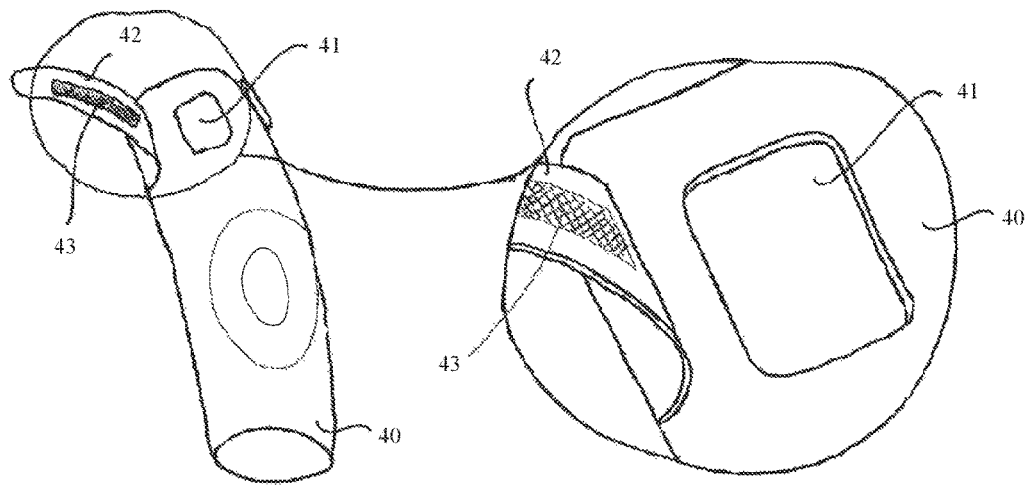
FIGS. 8, 8A, 9 and 10 illustrates another variant of the second embodiment.

In FIG. 7C, a local thickness 30' is used to properly apply the electrically active zone 5 against the skin of a user P is located on the strap 2 rather that on the electrically active zone (as is FIGS. 5-7B) the rest of the device being similar to the one represented in FIGS. 5-6.

In order to connect the conductive parts 25 (and the electrodes 28 or 31) to the stimulator (not shown in these figures) one may use wires or other equivalent means as described in relation to FIGS. 1-3 and the electrically active zone can be made of different equivalent ways, as taught in the present application.

Figure 9:
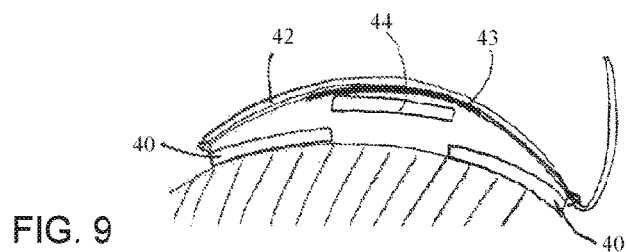
Figure 10:
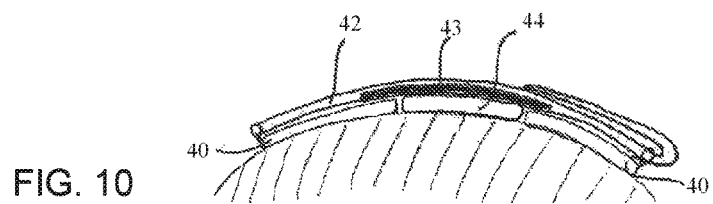

Another variant is illustrated in FIGS. 8, 8A, 9 and 10. In this second variant, the brace 40 also comprises an opening 41 and a strap 42 (as in the preceding variant). However, in this variant, the strap comprises an electrically active zone 43, for example an embroidered electrically active zone. As illustrated in FIGS. 9 and 10 (respectively an open and a closed configuration), the system further preferably comprises an additional electrically active zone 44 (for example a gel electrode having one or several conductive gel layers, or conductive paste) that is placed in the opening 41. The strap is closed over said electrically active zone 44 which then is in electrical contact with the zone 43 thus allowing an electrical treatment of the wearer. FIG. 9 shows the situation when the strap 42 is still open and FIG. 10 when the strap 42 is closed thus pressing the electrically active zone 44 between the zone 43 and the skin 45.

Preferably, the opening 21 or 41 is larger than the size of the electrode to allow a better positioning of the electrically active zone.

For connection of the zone 43 to a stimulator (not shown, but similar to the one illustrated in FIG. 1, reference 9), it is possible to use wires and other equivalent means, as for example described in relation to the preceding figures and embodiments of the present application.

Figure 11:
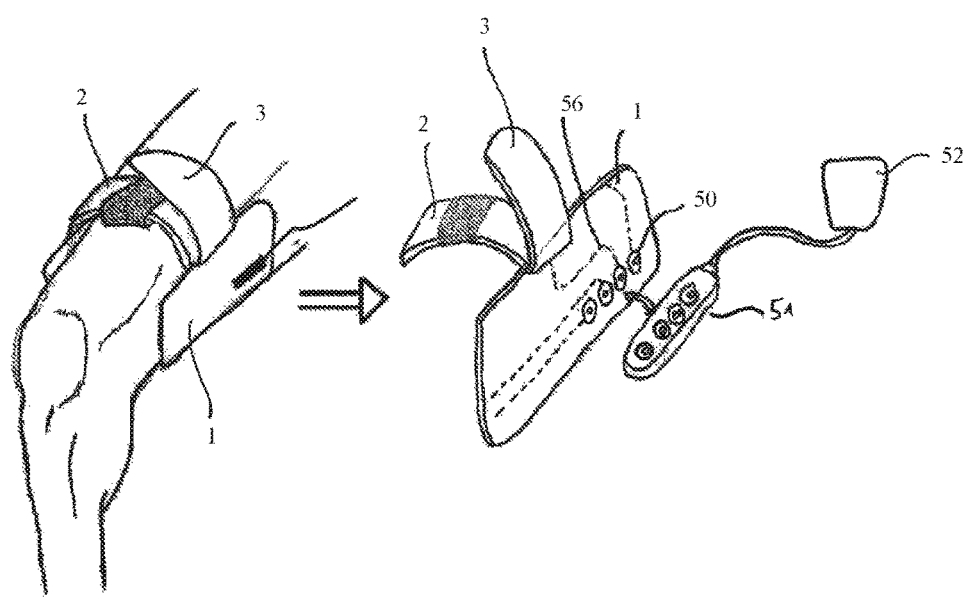
FIG. 11 illustrates the electric connection between the conductive electrode, the stripe, the brace and the stimulator.

In FIG. 11, one has represented a way to connect a stimulator to the brace. In this example, the brace 1 comprises a snap connector 50 cooperating with corresponding snap connector 51 itself connected to a stimulator 52. This facilitates the connection of the stimulator 52 and avoid errors in connection of wires. Of course, the connector could be made of any other kind of connector known on the market and the connection are liked to wire (for example wire 56) for the use of the device. For example, the wire 56 can be used for the electrical supply of the electrically active zone carried on the strap 2. Typically, the embodiment of FIG. 1 could be used with the snap connector system illustrated in FIG. 11 and the example of FIG. 11 can be transposed to the embodiment of FIG. 1.

Figure 12:
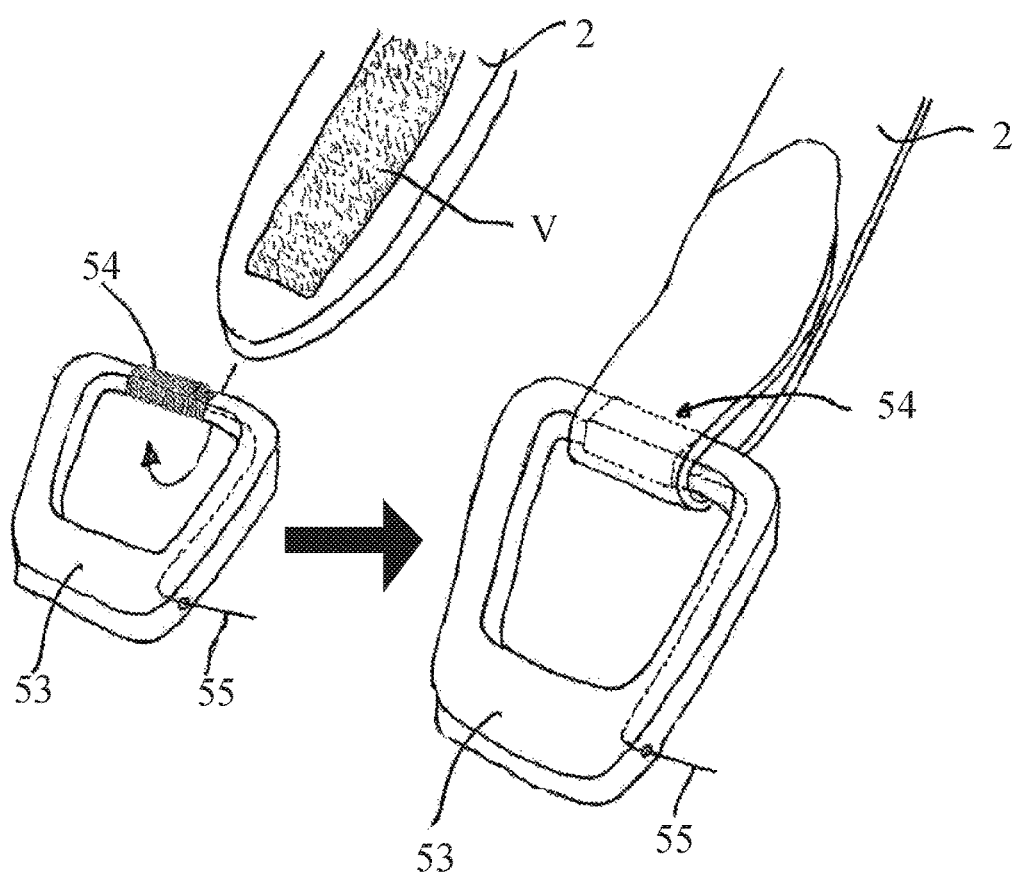
FIG. 12 illustrates a way of connecting the stripe to the brace.

FIG. 12 illustrates a variant to electrically connect the brace to the electrically active zones, this variant being applicable to all embodiments described in the present application. In this illustrative example, one uses a non-conductive (or isolated) buckle 53 with a conductive part 54 (for example a loop wire). In addition, there is a wire 55 that is connected to said conductive part. The strap 2 comprises a conductive embroidery or Velcro® V and passes over the conductive part 54 thus allowing an electrical contact. The strap 2 may be formed as in FIG. 2 or 2b with a wire (for example wire 13) for electrical contact with a support 6, 6' and finally the electrically active zone used for stimulation.

Of course other equivalents may be envisaged as well and the invention is not limited to the illustrative and exemplary embodiments and variants described herein. For example, the electrically active zones can be embroidered as described above, or other equivalent techniques may be used to form such active zones. They can be made of a conductive carbon layer, or another type of conductive layer that is attached to the brace, for example by snap connectors, Velcro®, gluing or other equivalent means.

In all the embodiments described above, the stimulator (9 or 52) may be connected to the electrodes or electrically active zones/pads through cables. When using cables, it may be advantageous to use connector (such as a snap connector) having one part attached to the brace (for example as illustrated in FIG. 11). This snap connector system may by asymmetrical to allow only one single connecting position and avoid errors.

In a further variant, it may be envisaged to connect directly the stimulator to an appropriate connection part attached to the brace. The stimulator will then be supported by the brace itself.

In order to measure values and evaluate said values, the use of the brace/device and also the state of recovery of the wearer, appropriate means are used, such as specific programs and measurements.

Also, although illustrative examples have been described as using conductive embroidered zones as electrically active zones, this should not be construed as limiting on the elements used as electrically active zones. They can be made of other means, for example conductive sheets, and other suitable equivalent means attached to the brace itself or to padding of the brace.

As can be understood from the above description, the present invention may be used as a stimulating device for the user with specific electrical stimulation being applied to the wearer of the brace through the electrically active zones, or also the same device made be used for electrical measurements on the user. Typically, some electrically active zones may be used for stimulation while other electrically active zones may be used for measurement.

In an embodiment, the electrically active zones may be used alternatively for stimulation or measurement.

In another embodiment, certain electrically active zones are used for measurements while a stimulation is carried out with other electrically active zones.

As one will readily understand, the measurement can be made via said electrically active zones, or it can be made via dedicated sensors, for example position sensors, motion sensors, displacement sensors and other equivalent sensors present on the brace or attached to the brace.

In such embodiments, the measured values can be brought back to the stimulator in a feedback loop to adapt the stimulation parameters used. In another variant, the measured values can be stored somewhere, for example in the stimulator or on a computer for subsequent analysis. The transmission of data can of course be made via wires or wireless. The subsequent analysis can be for example tracking of the effective use of the brace or other device being worn, correlation of the use and stimulation with improvements for the wearer, short, medium or long term analysis of the effectiveness of the brace or device being worn coupled with the electrical stimulation.

What is claimed is:

1. A system for electrical stimulation treatment of the body of a user, the system comprising:
   an electrode having at least one conductive layer;
   an orthopedic brace having
      an opening formed through a portion of the brace,
      an electrically conductive section comprising a conductive layer,
      a strap extending across the opening, the strap having an open configuration and a closed configuration, the strap configured to secure the electrode within the opening in the closed configuration such that the electrode contacts the electrically conductive section and the body of the user, and
      a non-conductive bottom layer and a non-conductive top layer, wherein the conductive layer of the electrically conductive section is positioned between the top layer and the bottom layer and disposed adjacent to the opening, wherein an edge of the bottom layer forms an edge of the opening, and an edge of the top layer is laterally spaced apart from the edge of the bottom layer so as to expose a portion of the conductive layer of the electrically conductive layer adjacent to the opening, and
   wherein the electrode is configured in size and shape to be received in the opening and secured by the closed configuration of the strap such that the electrode contacts the electrically conductive section of the orthopedic brace and the body of the user.

2. The system of claim 1, wherein the conductive layer of the brace is positioned between the top layer and the bottom layer on at least two opposite sides of the opening.

3. The system of claim 2, wherein the conductive layer of the brace comprises one of an embroidered conductive layer or a soft conductive layer.

4. The system of claim 3, wherein the conductive layer of the brace comprises a carbon layer.

5. The system of claim 2, wherein the electrode comprises a center portion with a first thickness and end portions with a second thickness at opposing ends of the electrode.

6. The system of claim 5, wherein the first thickness is greater than the second thickness.

7. The system of claim 6, wherein the center portion of the electrode is configured to be received in the opening and at least one of the end portions of the electrode is configured to be contact the conductive layer of the brace.

8. The system of claim 1, wherein the electrode further comprises a non-conductive layer attached to a first side of the conductive layer of the electrode and a strip of conductive gel attached to a second side of the conductive layer of the electrode, the strip of conductive gel positioned to contact the body of the user when the brace is worn by the user and the electrode is secured in the opening by the closed configuration of the strap.

9. The system of claim 8, wherein the conductive layer of the electrode is configured to contact the conductive layer of the brace and the strip of conductive gel is configured to be received in the opening when the electrode is secured by the strap.

10. The system of claim 1, wherein the electrode is deformable.

11. The system of claim 1, wherein the strap comprises a protruding section positioned over the opening, the protruding section configured to protrude at least partially into the opening when the strap is in the closed configuration.

12. The system of claim 1, wherein the electrically conductive section is in electrical connection with a stimulator, and wherein the electrode contacts the electrically conductive section so as to allow a stimulation signal to be transferred to the electrode via the electrically conductive section.

13. The system of claim 12, wherein the brace further comprises a snap connector for electrical connection of the brace to the stimulator.

* * * * *